United States Patent
Hopper et al.

(10) Patent No.: US 6,603,010 B2
(45) Date of Patent: Aug. 5, 2003

(54) SUPERNUCLEOPHILIC 4-SUBSTITUTED-PYRIDINE CATALYSTS, AND PROCESSES USEFUL FOR PREPARING SAME

(75) Inventors: Charles R. Hopper, Plainfield, IN (US); Ramiah Murugan, Indianapolis, IN (US); L. Mark Huckstep, Avon, IN (US); Eric F. V. Scriven, Greenwood, IN (US)

(73) Assignee: Reilly Industries, Inc., Indianapolis, IN (US)

( * ) Notice: Subject to any disclaimer, the term of this patent is extended or adjusted under 35 U.S.C. 154(b) by 0 days.

(21) Appl. No.: 09/993,046

(22) Filed: Nov. 6, 2001

(65) Prior Publication Data

US 2002/0165087 A1 Nov. 7, 2002

Related U.S. Application Data

(62) Division of application No. 09/463,902, filed as application No. PCT/US98/16024 on Jul. 31, 1998, now Pat. No. 6,369,230.
(60) Provisional application No. 60/055,086, filed on Aug. 1, 1997, and provisional application No. 60/054,473, filed on Aug. 1, 1997.

(51) Int. Cl.[7] ......................................... C07D 213/02
(52) U.S. Cl. ..................................................... 546/304
(58) Field of Search ........................................ 546/304

(56) References Cited

U.S. PATENT DOCUMENTS

| | | | |
|---|---|---|---|
| 3,452,018 A | 6/1969 | Santilli et al. ........... 260/256.5 |
| 3,509,165 A | 4/1970 | Ellzey, Jr. et al. .......... 260/295 |
| 4,012,437 A | 3/1977 | Shachat et al. ......... 260/482 R |
| 4,120,859 A | 10/1978 | Pluss et al. ............ 260/294.8 R |
| 4,148,797 A | 4/1979 | Plüss et al. ................. 546/344 |
| 4,150,232 A | 4/1979 | Pluss et al. ................. 546/339 |
| 4,158,093 A | 6/1979 | Bailey et al. ............... 542/455 |
| 4,279,579 A | 7/1981 | Froeschke ...................... 425/6 |
| 4,287,338 A | 9/1981 | McCall ....................... 544/123 |
| 4,588,522 A | 5/1986 | Blaschke et al. ........... 252/547 |
| 4,591,625 A | 5/1986 | Mathias ...................... 526/265 |
| 4,672,121 A | 6/1987 | Nummy ...................... 546/290 |
| 4,742,135 A | 5/1988 | Schulz et al. ............... 526/265 |
| 4,772,713 A | 9/1988 | Nummy ...................... 546/286 |
| 4,882,405 A | 11/1989 | Schulz et al. ............... 526/265 |
| 5,006,628 A | 4/1991 | Jackson, Jr. et al. ........ 528/182 |
| 5,136,092 A | 8/1992 | Borland et al. ................ 564/2 |
| 5,234,918 A | 8/1993 | Wissner et al. ............... 514/89 |
| 5,245,036 A * | 9/1993 | Robey et al. ............... 546/153 |
| 5,264,112 A | 11/1993 | Dahms ........................ 205/271 |
| 5,292,942 A | 3/1994 | Aigner et al. ................ 562/575 |
| 5,359,139 A | 10/1994 | Smith et al. .................... 564/2 |
| 5,371,250 A | 12/1994 | Seitz et al. .................... 554/70 |

FOREIGN PATENT DOCUMENTS

| WO | WO 93/08150 | 4/1993 | ......... C07C/53/126 |
|---|---|---|---|

OTHER PUBLICATIONS

U. Berg, R. Gallo and J. Metzger, "Demethylations Of Quanternary Pyridinium Salts By A Soft Nucleophile, Triphenylphosphine, Electronic And Steric Accelerations", *J. Org. Chem.*, vol. 41, No. 15, pp. 2621–2624 (1976).

H.J. Den Hertog, Jr., and J.P. Wibaut, "On The Bromination Of Pyridine In The Gaseous Phase At Elevated Temperatures", *Recueil des Travaux Chimiques des Pays–Bas*, vol. 4, No. 13, pp. 381–388 (1932).

T.–L. Ho, "Dequaternization Of Ammonium Salts By Nucleophiles", *Synthetic Communications*, vol. 3, No. 1, pp. 99–100 (1973).

D. Jerchel and L. Jakob, "Synthesen mit Pyridyl–pyridinium–halogeniden. Einführung der substituierten Aminogruppe in die 4–Stellung des Pyridinkerns", *Chemische Berichte*, vol. 91, No. 6, pp. 1266–1273 (1958).

J. P. Kutney and R. Greenhouse, "The Protection And Deprotection Of The Pyridine Nitrogen", *Synthetic Communications*, vol. 5, No. 2, pp. 119–124 (1975).

"A World Of Experience In Chemical Processing", *Sandvik Process Systems* brochure PS–488 ENG 4.96.

"Sandvik Rotoform® Process: Premium Pastilles at high production rates, low production costs", *Sandvik Process Systems* brochure PS–500 ENG 8.93.

* cited by examiner

*Primary Examiner*—Zinna Northington Davis
(74) *Attorney, Agent, or Firm*—Woodard, Emhardt, Moriarty, McNett & Henry LLP

(57) ABSTRACT

Described are preferred processes for producing extrusion-granulated supernucleophilic 4-amino-substituted pyridine catalysts, and granular products obtainable therefrom. Also described are preferred activation-substitution-deactivation processes for producing 4-aminopyridine compounds, which involve the use of acrylic acid or acrylamide or analogs thereof for activation, and substitution steps conducted under mild basic conditions in an excess of the amine reagent for 4-substitution. Such processes provide improved reacted masses which are more readily processed to recover the products in pure, heat-stable form. Further, described are processes for preparing 4-substituted-pyridines via pyridine betaines.

6 Claims, 2 Drawing Sheets

US 6,603,010 B2

SUPERNUCLEOPHILIC 4-SUBSTITUTED-PYRIDINE CATALYSTS, AND PROCESSES USEFUL FOR PREPARING SAME

REFERENCE TO RELATED APPLICATIONS

This application is a division of U.S. patent application Ser. No. 09/463,902 filed Apr. 13, 2000; now U.S. Pat. No. 6,369,230 which is the national stage of PCT/US98/16024 filed July 31, 1998; which claims priority to U.S. provisional patent application Nos. 60/055,086 and 60/054,473 both of which were filed Aug. 1, 1997, all of which are hereby incorporated by reference in their entirety.

BACKGROUND OF THE INVENTION

The present invention resides generally in the field of the preparation and use of 4-substituted pyridine compounds, and in particular to novel forms of supernucleophilic 4-substituted pyridine catalysts, and nucleophilic substitution processes useful for preparing such catalysts and other 4-substituted pyridines.

As further background, it is well known that many pyridines carrying an amino (desirably tertiary amino) group at the 4-position possess supernucleophilic properties making them highly advantageous for use as catalysts in acylation and other reactions. For example, the compound 4-N,N-dimethylaminopyridine (DMAP) is used on a large scale worldwide for acylation and other reactions in the pharmaceutical and agricultural industries. Historically, the preparation of 4-substituted pyridines such as DMAP has presented several challenges.

For example, tremendous research efforts worldwide have been made to discover effective means for transforming one group at the 4-position of the pyridine ring for another. Early on, researchers were hopeful that direct exposure of the free pyridine base to appropriate reagents would result in the effective modification of the 4-position. It has turned out, however, that most modifications of interest at the 4-position occur only at the cost of extreme conditions. For instance, 2-bromopyridine can be converted to 2-aminopyridine by reaction with ammonium hydroxide, but only at high temperatures of 200° C. and under pressure. Den Hertog et al., *Rec. Trav. Chim.*, 51, 381 (1932). Similarly, dimethylamine reacts with 4-chloropyridine only under pressure and at a temperature of 150° C. (L. Pentimalli, *Gass. Chem. Ital.*, 94, 902 (1964)), a process unsuitable for commercial scale. Likewise unsuitable for commercial scale is the reaction of sodium or potassium amide and metal methylanilides in etheral solvents or liquid ammonia, as described in Hauser, *J. Org. Chem.*, 15, 310 (1949). N-pyridyl-4-pyridinium chloride hydrochloride or 4-phenoxypyridine has been reacted with nucleophiles to displace at the 4-position (D. Jerchel et al., *Chem. Ber.*, 91, 1266 (1958)). However, these starting pyridine materials are far removed from commerce and thus such processes would be problematic if contemplated on a large scale.

In light of the difficulties of 4-substitution directly on the free base pyridine, a number of processes have been developed in which the 4-position (or 2-position) of the pyridine ring is activated toward nucleophilic substitution by a modification of the ring nitrogen of the pyridine. Such processes are generally known as activation-substitution-deactivation processes, and to date have involved either the N-oxidation or quaternization of the pyridine substrate, both of which are known to activate the 2- and 4-ring positions toward nucleophilic attack and expulsion of leaving groups at these positions. N-oxidation as a means to activate the 2- and 4-ring positions of pyridine has been relatively less studied than quaternization. This may be due to the fact that the level of activation imparted by N-oxidation is lower than that of quaternization. In the latter field, it is known that 4-substituted-pyridines such as 4-cyanopyridine can be quaternized with an alkyl iodide (e.g. methyl iodide) and reacted with ammonia to form a corresponding 4-aminopyridine. Metzger et al., *J. Org. Chem.*, 41 (15), 2621 (1978). The dequaternization of such alkyl quats, however, is problematic, as only relatively exotic reagents such as triphenylphosphene/dimethylformamide (Aumann et al., *J. Chem. Soc. Chem. Commun.*, 32, (1973)), triphenylphosphene/acetonitrile (Kutney et al., *Synth. Commun.*, 5 (2), 119 (1975)) and diazabicyclononane/dimethylformamide or thiourea (Ho, *Synth. Commun.*, 3, 99 (1973)) having been reported, with each of these processes inviting significant difficulty on an industrial scale.

More recently, research efforts have yielded quaternary-activated 4-substitution processes which can be practiced with greater advantage on a commercial scale. For example, U.S. Pat. No. 4,158,093 to Bailey et al. describes a route in which a 4-substituted pyridine base is quaternized with 2- or 4-vinylpyridine in the presence of a strong acid to yield a pyridylethyl quaternary salt. This activated quat form can then be subjected to nucleophilic substitution at the 4-position, and subsequently dequaternized in the presence of caustic.

U.S. Pat. Nos. 4,672,121 and 4,772,713 both to Nummy describe processes in which the 4-substituted pyridine base is reacted with acrylamide or an alkylacrylamide as the quaternizing reagent, and the resulting carbamoyl quat or a derivative therefrom is subject to nucleophilic displacement at the 4-position, again followed by dequaternization. In these '121 and '713 patents, the quaternization is conducted in the presence of a strong acid, and the substitution and dequaternization are conducted in the presence of a strong base such as alkali metal hydroxides or carbonates, or strong amidine bases.

The above-described research efforts have culminated in the past decade-and-a-half in the successful commercialization and worldwide use of the supernucleophilic catalyst, DMAP, and have opened the door to routes to similar useful 4-substituted pyridine compounds. However, needs remain for novel and improved 4-substitution processes for pyridines, and improved product forms. Desirable processes would entail the use of readily-available starting materials and reagents while providing high purity products and minimizing and/or simplifying purification steps. Improved processes would also minimize reagent use and the need to recycle materials or handle or dispose hazardous wastes. As well, new product forms, especially of supernucleophilic 4-substituted pyridine catalysts, would avoid or reduce difficulties which have been encountered in the handling of crystalline or flaked catalyst forms which have been available to date. The present invention provides several embodiments, each of which addresses one or more of these needs.

SUMMARY OF THE INVENTION

Accordingly, one feature of the present invention is the provision of a supernucleophilic 4-substituted pyridine catalyst in a unique form, and a process for making the same. The preferred process for preparing a granular supernucleophilic 4-substituted pyridine catalyst, especially a monoalkylamino- or dialkylaminopyridine catalyst, includes a step of providing the supernucleophilic catalyst as a molten flowable mass. This flowable mass is then extruded through an orifice into discrete liquid portions each corresponding to a granule to be formed. These liquid portions, in turn, are cooled to form a granular supernucleophilic catalyst. The granular supernucleophilic catalyst, most preferably 4-N,N-dimethylaminopyridine (DMAP), desirably has an average particular diameter of about 1 to about 10 mm. Suitable melt temperatures range from the melting point for the catalyst, e.g. 111–112° C. or DMAP, up to just below the decomposition temperature for the catalyst, with preferred melt temperatures ranging from about the melting point of the catalyst up to about 50° above that point, e.g. for DMAP about 112° C. to about 160° C., more preferably from the melting point up to about 30° C. above the melting point, and especially for DMAP about 115° C. to about 130° C.

In still more preferred processes, the extruding step is conducted using equipment optimally designed for forming the discreet portions. For example, such may involve an extrusion apparatus equipped to deliver the flowable mass through an orifice for a predetermined period of time to provide drops of the appropriate size. This control can be achieved, for example, by providing first and second wall members each having orifices, wherein the wall members are movable relative to one another to periodically align orifices in the first member with those in the second member for the predetermined period of time. The flowable mass is pressurized against the first wall member such that when the orifices in the first and second wall member are aligned, an amount of the flowable mass is extruded through the aligned orifices, for example downwardly onto a conveyor belt. Most preferred devices for these purposes include as the first member, a first container, e.g. a drum, filled and pressurized with the flowable mass, and as the second member a second container, e.g. a second drum, encasing the first container. Each container has orifices, and they are movable (e.g. rotatable) with respect to one another (preferably provided by a static inner container and a movable (rotating) outer container. Movement of the second container results in periodic alignment of the orifices for the predetermined time, during which the drops of supernucleophilic catalyst material are extruded through the aligned orifices and downwardly onto a passing conveyer. Such processes provide preferred, smooth-surfaced supernucleophilic catalyst granules of uniform size and shape, for example generally hemispherical in shape.

Another preferred embodiment of the invention provides a catalyst composition comprising a granulated supernucleophilic 4-(secondary or tertiary)aminopyridine catalyst, especially a dialkylaminopyridine catalyst such as DMAP. Preferred such catalysts have an average particle diameter of about 1 mm to about 10 mm, with most preferred catalyst forms having smooth granules of substantially uniform size and/or shape.

Additional preferred embodiments of the invention relate to improved activation-substitution-deactivation routes to 4-substituted pyridines. On such preferred embodiment involves a process for preparing a 4-(secondary or tertiary) aminopyridine compound. This process includes reacting a starting 4-substituted pyridine base having a leaving group as the 4-substituent, with an activating agent of the formula:

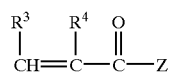

wherein $R^3$ and $R^4$, which may be the same as or may differ from one another, are each —H or a $C_1$–$C_4$ alkyl group, and Z is —$OR^7$ or $NR^5R^{6,}$ wherein $R^5$ and $R^6$, which may be the same as or may differ from one another, and may taken together form a ring, are each —H or $C_1$–$C_8$ alkyl; and $R^7$ is —H or $C_1$–$C_8$ alkyl. This reacting forms an activated 1,4-substituted pyridine, which is then reacted with a primary or secondary amine in at least a 3:1 molar ratio relative to the pyridine, to form a corresponding 1-substituted, 4-(secondary or tertiary)aminopyridine. The 1-substituted, 4-(secondary or tertiary)aminopyridine is then treated to remove the 1-substituent and thereby form a product medium including the 4-(secondary or tertiary) aminopyridine. It has been found that by conducting the substitution step in the presence of a large molar excess of the amine used as the nucleophile in the substitution, the use of strong bases such as alkali metal hydroxides in the substitution step can be minimized or eliminated, and that downstream product separations are simplified, providing highly pure, white 4-(secondary or tertiary) aminopyridine products even absent a solvent recrystallization step. This process is applied with preference to a manufacture of DMAP, wherein the amine is dimethylamine. The activating agent in this process is preferably acrylic acid or acrylamide.

Another embodiment of the present invention provides an activation-substitution-deactivation route to 4-nucleophile-substituted pyridines, wherein the activated pyridine species is a pyridine betaine. Preferred processes include reacting a starting 4-substituted pyridine base having a leaving group as the 4-substituent, with an α,β-unsaturated acid of the formula

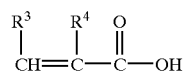

wherein $R^3$ and $R^4$, which may be the same as or may differ from one another, are each —H or a $C_1$–$C_4$ alkyl group, so as to form a corresponding activated 1,4-substituted pyridine betaine. The betaine is reacted with a nucleophile (Nu) to displace the leaving group and form a 1-substituted, 4-Nu-pyridine betaine. This betaine is then treated to remove the 1-substituent from the 4-Nu-pyridine compound. Preferred processes of this embodiment involve activation steps conducted in the absence of acid other than the α,β-unsaturated acid, and further the nucleophilic substitution is optionally conducted under mild basic conditions (i.e. in the absence of strong bases such as alkali metal hydroxide) in the presence of a primary or secondary amine used as the nucleophile in at least a 3:1 molar ratio relative to the pyridine betaine. In its most desirable form to date, this process involves the reaction of 4-cyanopyridine with acrylic acid to form a corresponding betaine. This betaine is reacted with dimethylamine to form a corresponding 4-N,N-dimethylaminopyridine betaine. This betaine is then treated in the presence of a strong base such as sodium hydroxide to remove the 1-substituent and form DMAP.

A still further embodiment of the invention provides a novel, optionally isolated, pyridine betaine of the formula

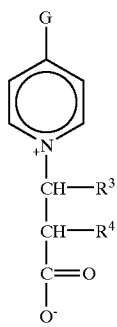

wherein:

G is a group selected from —CN and —NR$^1$R$^2$, wherein R$^1$ and R$^2$, which may be the same or may differ from one another, are each —H or a hydrocarbon group having from one to about ten carbon atoms, especially C$_1$–C$_{10}$ alkyl groups, and most preferably methyl groups; and R$^3$ and R$^4$, which may be the same as or may differ from one another, are selected from —H and C$_1$–C$_4$ alkyl groups.

A still further preferred embodiment of the invention provides heat stable 4-(secondary or tertiary)aminopyridine catalysts which may be produced by processes of the invention. Such heat stability can be exhibited in one or more of several ways. For example, preferred products, especially DMAP products, have an APHA color of less than about 50 and exhibit an increase in APHA color of no greater than about 50 when heated in a nitrogen atmosphere at about 120° C. for about 24 hours. For instance, more preferred DMAP products have an APHA color of less than about 10, and exhibit an APHA color of no greater than about 50 after heating in a nitrogen atmosphere at about 120° C. for about 24 hours. In another feature demonstrating heat stability, the present invention provides amorphous (i.e. non-crystalline form) 4-(secondary or tertiary)aminopyridine catalysts, particularly DMAP catalysts, having an APHA color of less than 20, more preferably less than 10.

The invention provides improved supernucleophilic catalysts and improved synthetic routes which can be used to prepare such catalysts and other useful substituted pyridines. The novel catalyst forms overcome handling and processing difficulties previously encountered with supernucleophilic catalysts, and preferred processes can be used to provide high yields while employing readily available materials, minimizing the use of reagents, and/or minimizing the difficulty and/or number of product purification steps. Additional objects, features and advantages of the invention will be apparent from the description that follows.

DESCRIPTION OF THE PREFERRED EMBODIMENTS

Figure 1:
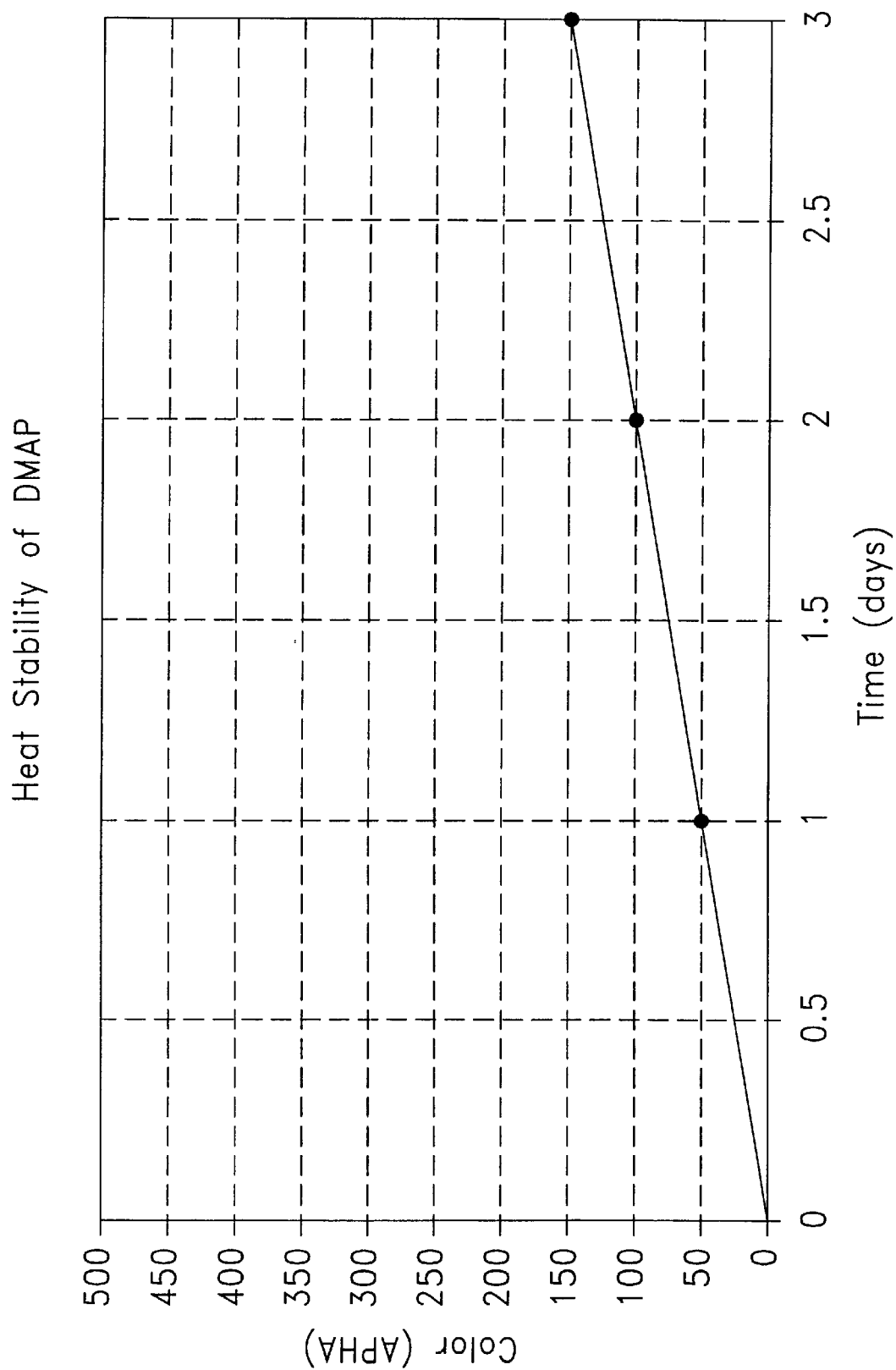
FIG. 1 is a graph of APHA color over time demonstrating heat stability of preferred DMAP product of the invention.

For the purposes of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As disclosed above, one preferred embodiment of the present invention provides novel forms of supernucleophilic catalysts. The novel forms in accordance with the invention are granular catalysts, and are preparable by melt extrusion processes which yield discreet liquid portions which upon solidification form smooth granules or prills.

Melt extrusion processes of the invention preferably involve the extrusion of molten 4-(secondary or tertiary) aminopyridine catalysts. Preferred catalysts for use in the invention thus include those of the formula:

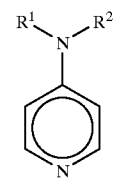

wherein R$^1$ and R$^2$, which may be the same as or may differ from one another, are each —H or a hydrocarbon group having from one to about ten carbon atoms, especially —H or a C$_1$–C$_{10}$ alkyl, with the proviso that at least one of R$^1$ and R$^2$ is a hydrocarbon group such as alkyl. More preferred catalysts occur where R$^1$ and R$^2$ are each alkyl, especially lower (C$_1$–C$_4$) alkyl such as methyl. The most preferred catalyst for melt extrusion processing in accordance with the invention is DMAP (i.e., R$^1$ and R$^2$ are both methyl).

As disclosed above, the catalyst is extruded, while molten, through an orifice in a fashion which provides granules of the desired size. Processes of the invention can, for example, be conducted in an extrusion apparatus as described in U.S. Pat. No. 4,279,579, which is hereby incorporated herein by reference in its entirety. Such an apparatus includes a first cylindrical container having a plurality of orifices and a second cylindrical container disposed within the first container and also including a plurality of orifices. Means are provided for admitting the flowable molten mass of catalyst into the second container, and means are also provided for producing relative rotation between the containers to periodically align the passages of the first container with the passages of the second container, so as to deposit drops of the flowable mass through the passages downwardly onto a conveyor belt also provided in the apparatus. Such processes in which discreet drops or portions are caused to solidify to form flowable granules are generally referred to as prilling processes, and the resulting granules are referred to as prills. In the preferred process, the conveyor belt is a cooled stainless steel belt, which hastens the solidification of the flowable mass drops as they exit the passage provided by the aligned orifices. Suitable devices for the conduct of such processes are commercially available from Sandvic Process Systems, Inc. of Totowa, N.J., U.S.A. Further information regarding such devices is available from Sandvic's trade literature, including that entitled Sandvik Rotoform® Process, Premium Pastilles at high production rates, low production costs (1993); A World of Chemical Experience in Chemical Processing: Sandvik Process Systems.

As indicated, the supernucleophilic catalyst is provided in a molten state for extrusion processing. Preferred melt processing temperatures will range from about the melting point of the catalyst up to the decomposition temperature of the catalyst. More Preferred temperatures will be at about the melting point up to about 50° C. above the melting point of the catalyst in hand. For the most preferred catalyst, DMAP, a generally suitable temperature range is about 112° C. to about 200° C., and a more preferred temperature range is about 115° C. to about 130° C. In any event, the temperature utilized will be selected in light of the conditions at hand, and will be optimized to provide the desired viscosity of the flowable catalyst mass for extrusion processing in accordance with the invention.

Granulated catalysts in accordance with the invention will preferably have smooth granules with an average particle diameter of about 1 to about 10 mm, more preferably about 1 to about 5 mm. In addition, preferred catalysts will have granules of substantially uniform shape and size. When produced by preferred extrusion processes as described above, granulated catalysts of the invention will have a substantially 3-dimensional shape (i.e. the deposited drops will solidify prior to their spreading to form a substantially 2-dimensional flake), which provides improved flow properties for the solid catalyst in accordance with the invention. Preferred granules so prepared will generally also have a relatively flat or planar surface on a first side (from contact with the conveyor belt), and a generally arcuate surface on a second side opposite the first side. Preferred granulated catalysts of the invention also exhibit desirable dissolution properties in aqueous medium, meaning that while provided in a readily handled and manipulated granulated Form in the dry state, once placed in aqueous media, the catalyst granules break up and dissolve into solution with relative ease and quickness, generally within about a few minutes with agitation at the catalytic levels at which they are conventionally used (e.g. at concentration levels less than about 10% by weight in solution). In addition, preferred granulated products of the invention will have a low level of fines having a particle diameter of less than about 600 microns, more preferably less than 5% by weight fines, and most preferably less than 3% by weight fines. Particle integrity of preferred products will also minimize the generation of fines under conditions of abrasion and impact. For example, preferred products will generate less than 10% by weight fines in friability testing under test methods S4-77 and/or S5-77 as described further in Example 9 below, more preferably less than 5% by weight generated fines and most preferably less than 2% by weight.

The preferred granulated catalysts of the invention are free-flowing, and exhibit little to no tendency to aggregate. These catalysts thus overcome difficulties which have been encountered with prior crystalline or flaked DMAP forms, and are advantageously handled in manufacturing, storage and use operations. As illustrations, catalysts of the invention demonstrate advantages making them well suited for transport operations including gravity flow or vacuum,(e.g. as in gravity flow addition or vacuum addition to reactors), and can optionally be packaged in containers adapted to facilitate such operations. For instance, in the case of gravity flow addition, granulated catalysts of the invention can be packaged in containers that are adapted for connection to reactor ports and that incorporate product release mechanisms that are activatable upon or after such connection. Such containers may also be adapted for efficient gravity flow of the granular catalyst out of an opening of the container, and in this regard may have a shape adapted to release all of the granular catalyst upon activation of the product release mechanism. To this end, the container may include one or more wall members inclined downwardly toward the opening of the container adapted for connection to the reactor port. In this manner, safe, efficient and convenient use of granular catalysts of the invention is facilitated.

The supernucleophilic catalyst material for use in preparing advantageous granules of the invention may be synthesized by any suitable route. For example, it may be prepared using activation-substitution-deactivation techniques described in any one of U.S. Pat. Nos. 4,158,093, 4,672,121 or 4,772,713, each of which is hereby incorporated by reference in its entirety. The supernucleophilic catalyst starting material may also be prepared by improved synthetic processes of the present invention as described below.

One preferred process of the invention involves activation-substitution-deactivation processes for preparing 4-substituted pyridine compounds, wherein the activating agent is an acrylic derivative or analog, and wherein the substitution step is conducted in the presence of a large excess of a secondary or tertiary amine ($HNR^1R^2$ wherein $R^1$ and $R^2$ are defined as above) used as the nucleophile to displace the leaving group during the substitution reaction.

Thus, in accordance with this process of the invention, a 4-L-substituted pyridine base, wherein L is a leaving group, will first be activated by reaction with an activating agent of the formula:

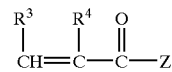

wherein $R^3$ and $R^4$, which may be the same as or may differ from one another, are each —H or a $C_1$–$C_4$ alkyl group, and Z is —$NR^5R^6$ or —$OR^7$ or, wherein $R^5$ and $R^6$, which may be the same as or may differ from one another, and may taken together form a ring, are each —H or $C_1$–$C_8$ alkyl; and $R^7$ is —H or $C_1$–$C_8$ alkyl.

Advantageous activation reactions will in general employ a molar excess of the activating agent relative to the pyridine base starting material to facilitate high levels of conversion. Accordingly, molar ratios of activating agent to pyridine base starting material will typically be in the range of 1.05:1 up to about 10:1, respectively, more typically in the range of about 1.05:1 to about 5:1. In addition, the activating agent may contain one or more polymerization inhibitors, in order to prevent unwanted polymerization. For example, the polymerization inhibitor may be MEAQ or a suitable thiazine compound such as phenylthiazine that is effective to prevent polymerization of the activating agents under distillative conditions.

The activation step is preferably performed in the presence of a strong acid catalyst (pKa less than 3), for example a strong organic acid, or a strong inorganic acid such as HCl, HBr, HI, sulfuric acid or phosphoric acid. Such acids will typically be used in a molar ratio of about 1–3:1 relative to the 4-L-substituted pyridine starting material, more preferably in a slight molar excess (e.g. in a molar ratio of about 1.05:1) relative to the pyridine starting material. The activation reaction is also preferably conducted under heated conditions, with temperatures in the range of about 50° C. to about 100° C. being typical, more preferably in the range of about 70° C. to about 80° C. The activation reaction can be conducted for several hours, with about 95%+ conversion being achieved in about four hours in more preferred inventive processes.

The concentration of the reaction during the activation step will vary in accordance with the particular reactants and reagents in hand, and the optimization of this parameter will be well within the skill of those practiced in a relevant field. Suitable reaction concentrations will generally provide reacted solutions containing about 10% to about 60% by weight of the activated pyridine intermediate, more typically in the range of about 30% to about 55% by weight.

Preferred products of such activation reactions will thus have the formula:

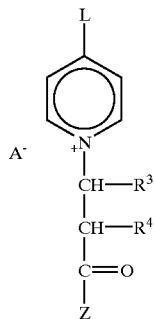

wherein:

Z, $R^3$ and $R^4$ are as defined above; and

A is an anion (provided, e.g., by the anion of the strong acid catalyst); and

L is a leaving group such as cyano, halo (fluoro, chloro, bromo, or iodo), arylsulfonyl having from six to ten carbon atoms, optionally substituted with one or more alkyl groups having from one to four carbon atoms; arylsulfonyloxy having from six to ten carbon atoms; alkylsulfonyloxy having from one to eight carbon atoms; aryloxy having from six to ten carbon atoms (e.g. phenoxy); arylthio having from six to ten carbon atoms (e.g. phenylthio); nitro, and the like.

In accordance with the invention, the activated 1,4-L-substituted pyridine formed in the activation step is then reacted in the presence of a primary or secondary amine charged n at least about a 2:1 molar ratio relative to the activated 1,4-substituted pyridine under mild (pH about 8 to about 10) basic conditions at the completion of combining the activated 1,4-substituted pyridine and the primary or secondary amine, most preferably at essentially the basic pH provided by the pyridine and primary or secondary amine reagents, i.e. in the substantial absence of any strong base such as sodium hydroxide in the reaction medium. In conducting this reaction, it is generally preferred to add the activated pyridine intermediate to an aqueous solution of the amine nucleophile, as this has been found to provide cleaner processes. Preferred amine nucleophiles for these purposes include those of the formula $HNR^1R^2$ wherein $R^1$ and $R^2$ are as defined above. Additional illustrative amines include hydrazine, alkylene diamines of up to eight carbon atoms, dialkylenetriamines of up to sixteen carbon atoms, polyethylenimines, and the like.

In contrast to prior known processes in which sodium hydroxide or similar bases have been used, it has been discovered that such strongly basic conditions can be avoided in the substitution step, and in so doing that cleaner reacted mediums are provided downstream, which are more readily processed to recover substantially pure 4-(secondary or tertiary)aminopyridines. More preferred substitution reactions are conducted in the presence of the primary or secondary amine in at least a 3:1 molar ratio relative to the pyridine compound, typically in about a 3–5:1 molar ratio. This reaction can be suitably conducted at room temperature (about 25° C.) or under heated conditions. For reactions at atmospheric pressure, preferred reaction temperatures will be room temperature up co about the boiling temperature for the lowest boiling component of the reaction mixture, typically the primary or secondary amine. For instance, in the manufacture of DMAP, the substitution reaction is typically conducted at temperatures of to about 60–70° C., as higher temperatures would begin to boil off the dimethylamine.

In the substitution reaction, the primary or secondary amine displaces the leaving group "L", losing a hydrogen atom in the process, so as to form an activated 1-substituted, 4-(secondary or tertiary)aminopyridine. The extent of completion of this reaction can be monitored and the process taken on to the deactivation phase upon achieving sufficient conversion. In the deactivation step, the 1-substituted, 4-(secondary or tertiary)aminopyridine is treated to remove the 1-substituent and thereby form a product medium including the 4-(secondary or tertiary)aminopyridine, e.g. of the formula:

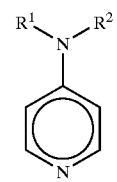

wherein $R^1$ and $R^2$ are as defined above.

As to conditions during the deactivation step, it is preferably conducted under basic, heated conditions. A strong base such as an alkali metal hydroxide can be used to advantage in facilitating the elimination of the 1-substituent. Desirable deactivations are also conducted at a temperature in the range of about 80° C. to about 100° C., although higher temperatures and superatmospheric pressures may also be employed.

As indicated above, it has been discovered that by conducting the substitution step in the presence of a large molar excess of the amine used as the nucleophile, the use of strong bases such as alkali metal hydroxides in the substitution step can be minimized or eliminated, and that downstream product separations are simplified, providing highly pure 4-(secondary or tertiary)aminopyridine products. For example, a typical reaction workup to recover the 4-(secondary or tertiary)aminopyridine product will involve an extraction of the reaction medium with a non-polar organic solvent such as toluene, to draw the 4-(secondary or tertiary)aminopyridine product into the organic solvent layer. The organic layer is then distilled to separate the pyridine product from the organic solvent, with the solvent typically having a lower boiling point and thus being collected first overhead. It has been found, in accordance with the invention, that in processes conducted as described above using mild basic conditions during the substitution step, the distillative separation is much cleaner. This provides a distinct separation of the pyridine product, which is collected overhead immediately as a relatively pure product, as opposed to encountering a need to collect a first, more crude pyridine product fraction, followed by a relatively pure fraction. Moreover, products can be obtained from such processes which are highly pure, as is exhibited for example by the recovery of white DMAP from the distillation step, even absent any subsequent solvent recrystallization. Such white products readily exhibit APHA colors of less than 50, and demonstrate superior thermal stability as compared to DMAP products prepared by other processes, as illustrated Example 4 below and its accompanying FIG. 1. It is thus advantageous to combine such processes with subsequent melt-processing of the product, without the need for any intervening crystallization. Suitable melt processing techniques include, for example flaking, or extrusion granulation processes as described above.

Another aspect of the present invention involves an activation-substitution-deactivation synthetic route to 4-substituted pyridines, in which the activated intermediate species is a pyridine betaine. Generally speaking, these inventive processes involve an activation step which includes reacting a starting 4-substituted pyridine base having a leaving group as the 4-substituent, with an α,β-unsaturated acid of the formula

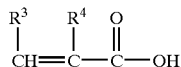

wherein $R^3$ and $R^4$, which may be the same as or may differ from one another, are each —H or a $C_1$–$C_4$ alkyl group, so as to form a corresponding activated 1,4-substituted pyridine betaine. The betaine is reacted with a nucleophilic agent (Nu-H) to displace the leaving group and form a 1-substituted, 4-Nu-pyridine betaine. This betaine is then treated to remove the 1-substituent and form the 4-Nu-pyridine compound.

The activation steps of such processes are conducted in a medium essentially free from acids other than the α,β-unsaturated acid, so as to enable the formation of the betaine intermediate as opposed to a quaternary salt intermediate incorporating a separate counterion coordinated with the positively-charged pyridine ring nitrogen. The activation steps are desirably conducted in a molar excess of the α,β-unsaturated acid to facilitate high and more rapid conversion of the pyridine base starting material to the betaine intermediate. Suitable molar ratios of α,β-unsaturated acid to pyridine base are about 1–5:1, respectively, with preferred ratios being about 1.1–3:1, respectively. These reactions are conducted with preference under heated conditions, for example at temperatures ranging from about 50° C. to about 100° C., more typically from about 50° C. to about 80° C.

Reaction concentrations during the activation step will again vary in accordance with the particular reactants and reagents in hand, and the optimization of this parameter will be well within the purview of those skilled in the relevant field. Suitable reaction concentrations will generally provide reacted solutions containing about 10% to about 50% of the activated pyridine intermediate, more typically in the range of about 30% to about 40% by weight.

The nucleophilic substitution reaction can be conducted in conventional fashion, e.g. in the presence of the nucleophilic reagent and added strong base. In so doing, it will generally be possible to use less strong base than in prior-known synthetic routes due to the absence of strong acid in the reaction medium residual from the activation step. Where the nucleophilic agent is itself basic (e.g. where it is a primary or secondary amine), as in above-described processes, the nucleophilic substitution step is desirably conducted under mild basic conditions (i.e. in the absence of strong bases such as alkali metal hydroxide) in the presence of the primary or secondary amine in at least a 2:1 molar ratio relative to the pyridine betaine, more preferably at least a 3:1 molar ratio, typically 3–5:1. As before, this substitution reaction can be suitably conducted at room temperature (about 25° C.) or under heated conditions.

The extent of completion of the substitution reaction can be monitored and the process taken on to the deactivation step upon achieving sufficient conversion to the 1-substituted, 4-Nu-pyridine intermediate. In the deactivation step, the 1-substituted, 4-(secondary or tertiary) aminopyridine is treated to remove the 1-substituent and thereby form a product medium including the 4-(secondary or tertiary) aminopyridine.

The deactivation step is preferably conducted under basic, heated conditions. As before, a strong base such as an alkali metal hydroxide and heat (e.g. about 50° C. to about 100° C.) can be used to advantage in facilitating the elimination of the 1-substituent to form the target 4-Nu-pyridine compound.

Illustrative processes of this embodiment of the invention utilize 4-substituted pyridine starting materials encompassed by the formula:

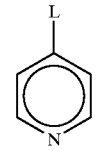

wherein L is a leaving group such as cyano, halo (fluoro, chloro, bromo, or iodo), arylsulfonyl having from six to ten carbon atoms, optionally substituted with one or more alkyl groups having from one to four carbon atoms; arylsulfonyloxy having from six to ten carbon atoms; alkylsulfonyloxy having from one to eight carbon atoms; aryloxy having from six to ten carbon atoms (e.g. phenoxy); arylthio having from six to ten carbon atoms (e.g. phenylthio); nitro, and the like. This starting pyridine is reacted as described above with the α,β-unsaturated acid to form a pyridine betaine intermediate of the formula:

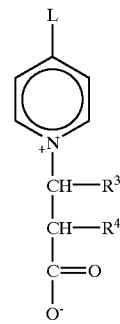

wherein L, $R^3$ and $R^4$ are as defined above. This betaine is then subjected to a nucleophilic substitution reaction with a nucleophilic reagent, Nu-H, of sufficient strength to displace the leaving group, L, and form a second pyridine betaine intermediate of the formula:

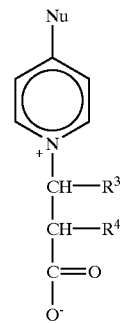

In turn, this intermediate is treated to remove the 1-substituent, e.g. in the presence of caustic and heat, to form a 4-substituted pyridine product of the formula:

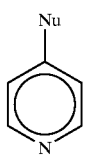

More preferred processes of this embodiment of the invention are provided where L is cyano, the nucleophile is HNR¹R² wherein R¹ and R² are as defined above, resulting in a 4-substituted pyridine product of the formula:

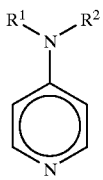

wherein $R^1$ and $R^2$ are as defined above. These processes provide clean distillative separations to recover highly pure 4-substituted pyridines, which can be taken on to melt processing (e.g. flaking or melt extrusion as described above) without intervening recrystallization, to provide high quality product forms.

In its most desirable form to date, this betaine-mediated process involves the reaction of 4-cyanopyridine with acrylic acid to form a corresponding pyridine betaine. This betaine is reacted with dimethylamine to form a corresponding 4-N,N-dimethylaminopyridine betaine. This betaine is then treated in the presence of a strong base such as sodium hydroxide to remove the 1-substituent and form DMAP. Such a process is illustrated in Scheme 1 below:

SCHEME I

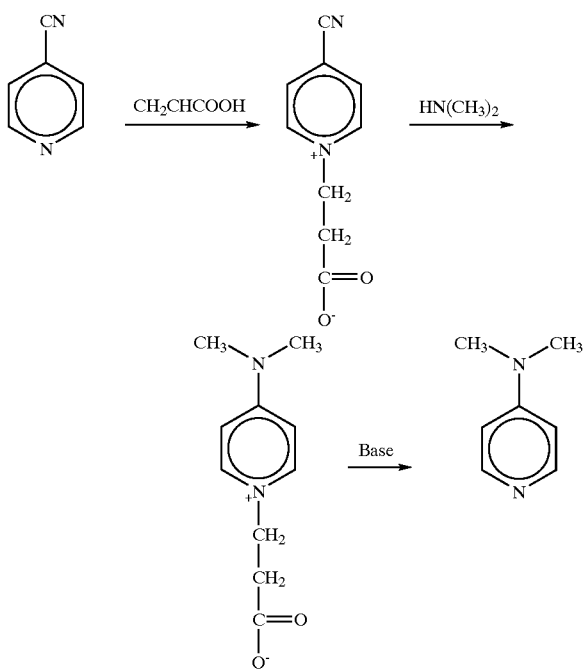

These processes provide substantial savings in reagents due to the absence of strong acid in the activation step, and the consequent reduced requirements for base during the substitution and/or dequaternization steps. In addition, DMAP products produced by such betaine-mediated processes are highly white as recovered from extraction/distillation steps as described above, and provide advantageous melt-processed processed product forms readily having APHA colors of less than about 50.

Activation-substitution-deactivation processes of the invention as discussed-above can be conducted for example in batch or continuous modes. In continuous modes, the processes may occur in continuous stirred tank reactors, tube reactors, or the like. In one preferred form, three continuous reaction zones can be established to carry out the activation, substitution, and deactivation steps, respectively. For example, tube reactors may be utilized wherein the 4-L-substituted pyridine starting material, especially 4-cyanopryridine, activating agent, and optionally strong acid such as HCl are combined in a tube reactor and allowed to react to form the 4-L-substituted quat or betaine intermediate. In another continuous zone, e.g. in another tube reactor, the nucleophile (Nu) to substitute for the 4-L-substituent can be combined with the intermediate, and the reaction to form the 4-Nu-substituted intermediate caused to proceed. In a still further zone, e.g. a still further tube reactor, a base (e.g. aqueous alkali or alkaline earth metal hydroxide such as NaOH) can be combined with the stream containing the 4-Nu-substituted intermediate to deactivate the intermediate and form the desired 4-Nu-substituted pyridine compound. Heat exchangers can also be used to control the heat of the reactants in, after or between the zones. For example, heat exchangers can be included to add heat between the activation and substitution zones and/or between the substitution and deactivation zones. Still further, continuous recovery operations can be performed to recover the product as it exits the continuous reaction zones. For instance, a continuous extractor can be incorporated into the continuous processing after the 4-Nu-pyridine product has been formed, to extract the product from the aqueous chase present into an organic phase. In most preferred continuous processes, the product is DMAP, the 4-L-substituted pyridine is 4-cyanopyridine, and the nucleophile is dimethylamine.

For purposes of promoting a further understanding of the present invention and its advantages, the following specific Examples are provided. It will be understood that these Examples are illustrative, and not limiting, of the present invention.

EXAMPLE 1

Production of 4-Dimethylaminopyridine via Acrylic Acid Quat

4-Cyanopyridine (300 gm, 2.882 mole) and 32% aqueous hydrochloric acid (342.3 gm, 3.024 mole) were combined and 50% aqueous acrylic acid (415.2 gm, 2.881 mole) added to the mixture with stirring. The combined reactants were heated with stirring for four (4) hours at 70° C. The resulting reacted mixture was then added to a 40% aqueous solution of dimethylamine (893.6 gm, 995 ml, 7.929 mole) with continued heating and stirring for one (1) hour at 40° C. Fifty percent (50%) aqueous sodium hydroxide (923.5 gm. 620 ml) was added to the reaction mixture with continued stirring and the temperature increased and maintained at 90° C. for one (1) hour. The reaction mixture was cooled to 70° C. and extracted with toluene (150 ml). After separation of layers, the aqueous layer was extracted with a second portion of toluene (100 ml). The toluene layers were combined and distilled. Toluene was removed at atmospheric temperature and 4-dimethylaminopyridine distilled at reduced pressure (b.p. 190° C., 150 mmhg) to give 4-dimethylaminopyridine (299.3 gm, 2.4497 mole).

EXAMPLE 2

Production of 4-Dimethylaminopyridine via Acrylic Acid Betaine

A. Betaine Synthesis

A one liter, four neck flask was equipped with a mechanical stirrer, thermometer, and a reflux condenser. The flask was charged with 4-cyanopyridine (150.0 g, 1.441 mole), water (360.0 g), and acrylic acid (166.2 g, 2.306 mole). The reaction mixture was heated to 70–75° C. and held for 5 to 8 hours. Reaction mixtures were then allowed to cool to room temperature and stirred overnight, or in some cases, over a weekend before analysis by NMR. The conversion was determined by ratioing the ring protons of the betaine with those of unreacted 4-cyanopyridine, the limiting reagent.

B. DMAP Synthesis

A two liter, four neck flask was equipped with a mechanical stirrer, reflux condenser, thermometer, and an addition funnel. The flask was charged with 40% dimethylamine solution (488.2 g, 4.331 mole). With good agitation, the above betaine solution (673.3 g) was added to the DMA allowing the reaction temperature to reach 45° C. max. The reaction mixture was stirred for about 15 minutes. The reaction mixture was then heated to about 70° C. and 50% NaOH (576.8 g, 7.21 mole) was slowly added. As the NaOH was added, DMA was evolved from the condenser and the temperature was held to 70–80° C. Upon completion of the NaOH addition, the reaction mixture was heated to reflux and held for one hour to spring the betaine. Alternatively, the DMAP betaine solution, at about 45° C., has been placed under reduced pressure (water aspirator) and the NaOH was slowly added at the lower temperature. After the NaOH addition was complete, the reaction mixture was heated to 70° C., while still under vacuum, to remove the DMA. At 70° C., the vacuum was released and the reaction mixture heated to reflux and held for 1 to 2 hours. The hot reaction mixture, regardless of which method of DMA removal was used, was cooled to about 90° C. and extracted with toluene (2×150 ml) at 70–80° C. The layers were separated and the top layers (401.4 g) were combined for distillation. The toluene was removed by atmospheric distillation until the pot temperature was 180° C. The pot was slowly eased under vacuum to a pressure of about 110 mm Hg. The DMAP was distilled at a head temperature of about 185–190° C. until the pot was essentially dry. The DMAP distillate (136.0 g, 1., 113 mole) represented a 77.3% yield. The distillate was crystallized from toluene as a 40 wt % solution. The crystallized product was recovered using a lab centrifuge and dried in a vacuum oven. The dried material (118.1 g, 0.967 mole) represented a 67.1% yield of crystallized material.

EXAMPLE 3

Production of 4-Dimethylaminopyridine via Acrylamide Quat

4-Cyanopyridine (300 gm, 2.882 mole) and 32% aqueous hydrochloric acid (342.3 gm, 3.024 mole) are combined and 50% aqueous acrylamide (2.881 mole) added to the mixture with stirring. The confined reactants are heated with stirring for four (4) hours at 70° C. A 40% aqueous solution of dimethylamine (893.6 gm, 995 ml, 7.929 mole) is added to the mixture with continued heating and stirring for one (1) hour at 40° C. Fifty percent (50%) aqueous sodium hydroxide (923.5 gm. 620 ml) is added to the reaction mixture with continued stirring and the temperature increased and maintained at 90° C. or one (1) hour. The reaction mixture is cooled to 70° C. and extracted with toluene (150 ml). After separation of layers, the aqueous layer is extracted with a second portion of toluene (100 ml). The toluene layers are combined and distilled. Toluene is removed at atmospheric temperature and 4-dimethylaminopyridine distilled at reduced pressure (b.p. 190° C., 150 mmhg) to give DMAP.

EXAMPLE 4

Heat Stability Studies for DMAP

In this Example, a DMAP sample was produced essentially as described in Example 1 hereof. The sample was heated to 120–130° C., under nitrogen, and held for three days. Samples were taken on a daily basis to test for color degradation. The results are shown in FIG. 1. As can be seen, the product of Example 1 hereof had superior heat stability, having an APHA color of only 50 after 24 hours and of only about 150 after three days under these molten conditions.

Similar testing of the product of Example 3 hereof reveals that it also possesses superior heat stability properties.

EXAMPLE 5

Preparation of Melt-Extruded DMAP Granules

A sample of 4-dimethylaminopyridine was molten, at a temperature of 115–125° C. The molten material was deposited dropwise onto a smooth, porcelain surface. The drops solidified rapidly and formed granules which were generally hemispherical in shape. The granulated product was removed from the surface and charged to a glass container (leaving substantial head space) and observed for particle integrity and flow properties. Upon agitation of the container it was found that the granules were resistant to fracture and highly free-flowing, exhibiting little or no tendency to adhere to one another.

EXAMPLE 6

Automated Melt-Extrusion of DMAP Granules

4-N,N-Dimethylaminopyridine (DMAP) is produced as described in Example 1. The 4-N,N-dimethylaminopyridine distillate is maintained in the molten state and is processed as follows (without recrystallization). The molten DMAP distillate is maintained in a storage tank under a nitrogen atmosphere. The storage tank is connected as feed to a melt extrusion apparatus, e.g., such as one available from Sandvik Process Systems, Inc., Totowa, N.J., USA, and/or described in U.S. Pat. No. 4,279,579. The apparatus includes a rotating drum with orifices through which the molten product is extruded into discrete liquid portions downwardly onto a moving, cooled stainless steel conveyor belt. The speed and direction of the belt are synchronized with the linearized speed and direction of the orifices of the rotating drum, to provide efficient and uniform deposit of the molten material onto the belt. The extrusion orifices are approximately 1 mm in diameter, leading to approximately 2 to 5 mm diameter granules. The melt extrusion apparatus is operated with the DMAP at a temperature of approximately 120–130° C., and the DMAP is preferably maintained at this temperature through storage and extrusion processing or no longer than about 8 hours. The resulting, generally hemispherical DMAP granules have good color (APHA color of about 100 or less), are hard, and have smooth surfaces. The granules are resistant to fracture and have substantial non-caking properties.

EXAMPLE 7

Automated Melt-Extrusion of DMAP Granules

The process of Example 6 is repeated, except that the 4-dimethylaminopyridine used is prepared via the acrylamide route described in Example 3. Again, the product granules have good color, integrity, and flow properties.

EXAMPLE 8

Automated Melt-Extrusion of DMAP Granules

In this example a Rotoformer available from Sandvik Process Systems, Inc., Totowa, N.J., USA, was used to prepare melt-extruded DMAP granules (prilled form). This machine generally has the features described U.S. Pat. No. 4,279,579, and is also described in Sandvik Rotoform® Process, Premium Pastilles at high production rates, low production costs (1993); A World of Chemical Experience in Chemical Processing: Sandvik Process Systems.

Figure 2:
FIG. 2 is enlarged digital image of a photograph of a preferred granular DMAP catalyst product of the invention.

The bore size on the rotating shell of the rotoformer was 1.5 mil. DMAP, prepared generally as described in Example 1, was maintained as a melt at about 120° C.–140° C. for feed to the rotoformer. During operation of the machine, molten DMAP was extruded through the bores onto the cooled belt of the rotoformer, providing DMAP prills having diameters of about 1–4 mil. The prills were removed at the end of the belt by a micarta laminated plastic blade, at which point the prills exhibited a temperature of about 30° C. A digital image of a photograph of representative DMAP prills is presented as FIG. 2. Upon inspection, the prills were found to be substantially uniform in shape and to exhibit excellent hardness and integrity. The prills also exhibited little or no tendency to cake.

EXAMPLE 9

Friability Testing of DMAP Prills

DMAP prills prepared as in Example 8 were subjected to friability testing under procedures commonly used to test sulfur and other like particulates. In particular, the prills were tested under the procedures of test methods S4-77 and S5-77. These and other test methods identified in this Example were performed as described in Sampling and Testing Sulphur Forms, published by the Sulphur Derivatives Institute of Canada, Box 9505 Bloy Valley Square 1, 830-202 Sixth Avenue, Calgary, Alberta, Canada T2P2W6. For the S4-77 method, prilled DMAP samples were oven dried at 50° C. plus or minus 5° C. to constant weight, weighed to the nearest 0.1 and air cooled. The samples were then transferred co a tumbler having a diameter of 250 mm and rotated at a speed of 19 rpm plus or minus 1 rpm for a total of 450 revolutions, maintaining a substantially uniform peripheral speed. After the prescribed revolutions, the material was cleaned from the tumbler and its weight recorded. The material was then subjected to dry sieve analysis to determine particle size distribution. The results are set forth in Table 1.

TABLE 1

| Sieve Size | Original Sample Percent Retained | | Tumbled Sample Percent Retained | |
|---|---|---|---|---|
| μm | Individual | Cumulative | Individual | Cumulative |
| 4750 | 0.00 | 0.00 | 0.00 | 0.00 |
| 3350 | 0.12 | 0.12 | 0.05 | 0.05 |
| 2360 | 14.40 | 14.52 | 8.50 | 8.54 |
| 2000 | 48.75 | 63.27 | 48.96 | 57.50 |
| 1180 | 26.05 | 89.32 | 29.06 | 86.56 |
| 600 | 7.64 | 96.97 | 10.31 | 96.87 |
| 300 | 1.68 | 98.65 | 2.61 | 99.48 |
| <300 | 1.35 | 100.00 | 0.52 | 100.00 |
| Total | 100.00 | 462.87 | 100.00 | 449.00 |
| Fineness Factor (FF)* | $FF_o = 4.63$ | | $FF_t = 4.49$ | |

Fineness Factor (FF) = Total Cumulative % retained/100
Fines (particle size <300) Content, (Original Sample) = 1.3%
Fines Production = 0.03%
Particle Breakdown Modulus (PBM) = $(FF_o - FF_t)/FF_c \times 100 = 2.99\%$.

In the S5-77 test method, a cylindrical tumbler having a diameter of 711 mm and length of 508 mm was used. The tumbler had a 89 mm wide shelf mounted within along the entire length of the cylinder. The tumbler was rotated 40 times at a speed of 31 rpm plus or minus 1 rpm. The sample was then collected and subjected to dry sieve analysis as in the S4-77 method discussed above. The results are presented in Table 2.

TABLE 2

| Sieve Size | Original Sample Percent Retained | | Tumbled Sample Percent Retained | |
|---|---|---|---|---|
| μm | Individual | Cumulative | Individual | Cumulative |
| 4750 | 0.00 | 0.00 | 0.00 | 0.00 |
| 3350 | 0.12 | 0.12 | 0.01 | 0.01 |
| 2360 | 14.40 | 14.52 | 7.82 | 7.83 |
| 2000 | 48.75 | 63.27 | 48.40 | 56.23 |
| 1180 | 26.05 | 89.32 | 31.44 | 87.67 |
| 600 | 7.64 | 96.97 | 9.65 | 97.32 |
| 300 | 1.68 | 98.65 | 2.08 | 99.39 |
| <300 | 1.35 | 462.87 | 0.61 | 100.00 |
| Total | 100.00 | 462.87 | 100.00 | 448.44 |
| Fineness Factor (FF)* | $FF_o = 4.63$ | | $FF_t = 4.48$ | |

Fineness Factor (FF) = Total Cumulative % retained/100
Fines (particle size <300) Content, Original Sample = 1.3%
Fines Production = 0.6%
Particle Breakdown Modulus (PBM) = $(FF_o - FF_t)/FF_c \times 100 = 3.12\%$.

The data presented in Tables 1 and 2 demonstrate that the prilled DMAP form not only has a low initial fines content but also exhibits unexpectedly good particle integrity and resistance to fracture and fines production under conditions of abrasion and impact.

The invention has been described above in detail, with specific reference to its Preferred embodiments. It will be understood, however, that a variety of modifications and additions can be made to the procedures disclosed without departing from the spirit and scope of the invention. Such modifications and additions are desired to be protected. In addition, all publications cited herein are indicative of the level of skill in the relevant art, and are each hereby incorporated by reference each in their entirety as if individually incorporated by reference and fully set forth.

What is claimed is:

1. A heat stable 4-(secondary or tertiary)aminopyridine catalyst which has an APHA color of less than about 50 and exhibits an increase in APHA color of no greater than about 50 when heated in a nitrogen atmosphere at about 120° C. for about 24 hours.

2. The catalyst of claim 1 which is 4-N,N-dimethylaminopyridine.

3. The catalyst of claim 2, which has an APHA color of less than about 10, and exhibits an APHA color of no greater than about 50 after heating in a nitrogen atmosphere at about 120° C. for about 24 hours.

4. An amorphous 4-(secondary or tertiary)aminopyridine catalyst having an APHA color of less than 20.

5. The catalyst of claim 4 which is 4-N,N-dimethylaminopyridine.

6. The catalyst of claim 5, having an APHA color of less than 10.

* * * * *